(12) United States Patent
Ganatra et al.

(10) Patent No.: US 8,700,132 B2
(45) Date of Patent: Apr. 15, 2014

(54) SYSTEMS AND METHODS FOR NAVIGATION WITHIN A BRANCHED STRUCTURE OF A BODY

(75) Inventors: Jenelle M. Ganatra, Eagleville, PA (US); Juerg Tschirren, Iowa City, IA (US); John T. Garber, II, Westport, CT (US)

(73) Assignee: Vida Diagnostics, Inc., Iowa City, IA (US)

( * ) Notice: Subject to any disclaimer, the term of this patent is extended or adjusted under 35 U.S.C. 154(b) by 0 days.

(21) Appl. No.: 13/495,858

(22) Filed: Jun. 13, 2012

(65) Prior Publication Data

US 2012/0283558 A1 Nov. 8, 2012

Related U.S. Application Data

(63) Continuation of application No. 12/043,518, filed on Mar. 6, 2008, now Pat. No. 8,219,179.

(51) Int. Cl.
*A61B 5/05* (2006.01)

(52) U.S. Cl.
USPC ........................................................ 600/424

(58) Field of Classification Search
USPC ......... 600/101, 117, 160, 407, 410, 414, 415, 600/416, 423, 424, 426, 429, 433, 434, 462, 600/475
See application file for complete search history.

(56) References Cited

U.S. PATENT DOCUMENTS

| | | | |
|---|---|---|---|
| 5,558,091 A | 9/1996 | Acker et al. | |
| 6,380,732 B1 | 4/2002 | Gilboa | |
| 6,456,868 B2 | 9/2002 | Saito et al. | |
| 6,466,687 B1 | 10/2002 | Uppaluri et al. | |
| 6,466,815 B1 | 10/2002 | Saito et al. | |
| 6,558,333 B2 | 5/2003 | Gilboa et al. | |
| 6,580,938 B1 | 6/2003 | Acker | |

(Continued)

FOREIGN PATENT DOCUMENTS

| | | |
|---|---|---|
| DE | 102005039657 A1 | 3/2007 |
| WO | 03007198 A2 | 1/2003 |
| WO | 03086498 A2 | 10/2003 |
| WO | 2005119505 A2 | 12/2005 |

OTHER PUBLICATIONS

PCT/US2009/036281, International Search Report and Written Opinion dated Aug. 19, 2009.

(Continued)

*Primary Examiner* — Unsu Jung
*Assistant Examiner* — Michael N Fisher
(74) *Attorney, Agent, or Firm* — Fredrikson & Byron, P.A.

(57) ABSTRACT

A system and method for navigating a medical instrument in a branched structure of a body employs a tracking system, for collecting positional information for the medical instrument, and data, which defines a geometrical model of the branched structure, in particular, coordinates for predetermined points defining a pathway extending along branches of the model. Coordinates are identified for each Euclidean distance of the instrument, from an anchor point of a coordinate system for the tracking system, that corresponds to a Euclidean distance of a designated point, of the predetermined points, from a reference point of a coordinate system for the model, wherein the anchor point of the tracking coordinate system has been established to correspond to the reference point of the model coordinate system. The two coordinate systems are registered to one another using the identified coordinates of the instrument and the corresponding coordinates of each designated point.

18 Claims, 9 Drawing Sheets

(56) References Cited

U.S. PATENT DOCUMENTS

| | | | |
|---|---|---|---|
| 6,615,155 B2 | 9/2003 | Gilboa | |
| 6,711,429 B1 | 3/2004 | Gilboa et al. | |
| 6,775,404 B1 | 8/2004 | Pagoulatos et al. | |
| 7,233,820 B2 | 6/2007 | Gilboa | |
| 7,274,810 B2 * | 9/2007 | Reeves et al. | 382/128 |
| 7,760,941 B2 * | 7/2010 | Bornemann et al. | 382/173 |
| 2003/0029464 A1 | 2/2003 | Chen et al. | |
| 2003/0108853 A1 * | 6/2003 | Chosack et al. | 434/262 |
| 2005/0182295 A1 * | 8/2005 | Soper et al. | 600/117 |
| 2005/0228250 A1 * | 10/2005 | Bitter et al. | 600/407 |
| 2005/0251017 A1 | 11/2005 | Azar | |
| 2005/0272971 A1 * | 12/2005 | Ohnishi et al. | 600/101 |
| 2006/0030958 A1 | 2/2006 | Tschirren et al. | |
| 2007/0053562 A1 | 3/2007 | Reinhardt et al. | |
| 2007/0078334 A1 | 4/2007 | Scully et al. | |
| 2007/0092864 A1 | 4/2007 | Reinhardt et al. | |
| 2007/0223794 A1 * | 9/2007 | Preiss et al. | 382/128 |
| 2007/0293721 A1 * | 12/2007 | Gilboa | 600/117 |

OTHER PUBLICATIONS

Tschirren, Juerg, et al., "Matching and anatomical labeling of human airway tree", IEEE Transactions of Medical Imaging, pp. 1-8, 2005, work was supported in party by NIH grant HL-064368.

Tschirren, Juerg, et al., "Intrathoracic Airway Trees: Segmentation and Airway Morphology Analysis from Low-Dose CT Scans", IEEE Transactions on Medical Imaging, pp. 1-11, 2005, work was supported in part by NIH grant HL-064368.

Li, Kang, "Efficient Optimal Net Surface Detection for Image Segmentation—From Theory to Practice", Masters Thesis for University of Iowa, Dec. 2003.

Tschirren, Juerg, "Segmentation, Anatomical Labeling, Branchpoint Matching, and Quantitative Analysis of Human Airway Trees in Volumetric CT Images", Doctors Thesis for University of Iowa, Aug. 2003.

Tschirren, Juerg, "Segmentation, branchpoint matching, and anatomical labeling of human airway trees in volumetric CT images", Ph.D. Defense Presentation, University of Iowa, Jul. 10, 2003.

Leotta, Daniel F., "An Efficient calibration Method for Freehand 3-D Ultrasound Imaging Systems", May 13, 2004, pp. 999-1008, vol. 30, No. 7, Ultrasound in Medicine & Biology, (doi:10.1016/j.ultrasmedbio.2004.5.007).

Horn, Berthold K. P., "Closed-form solution of absolute orientation using unit quartemions", Journal of the Optical Society of America A, Apr. 1987, pp. 629-642, vol. 4.

* cited by examiner

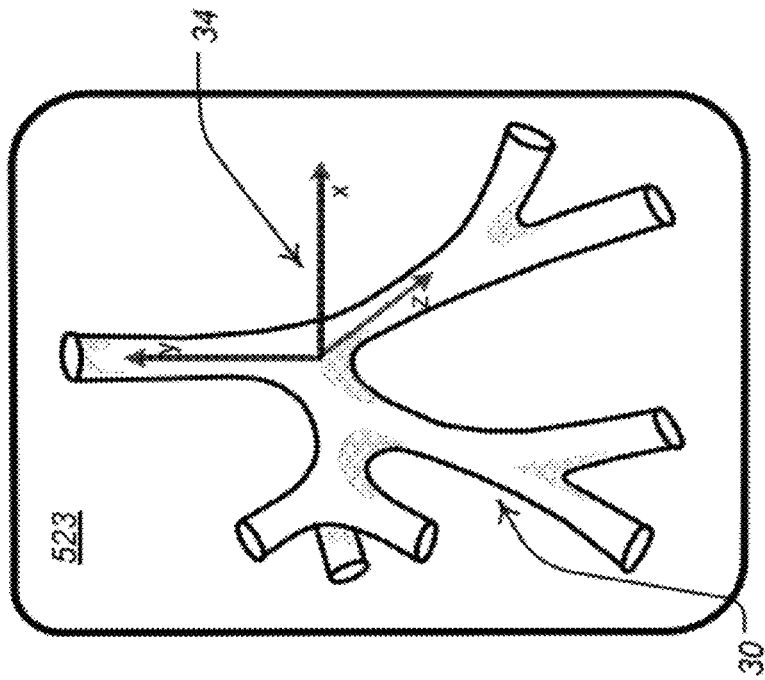
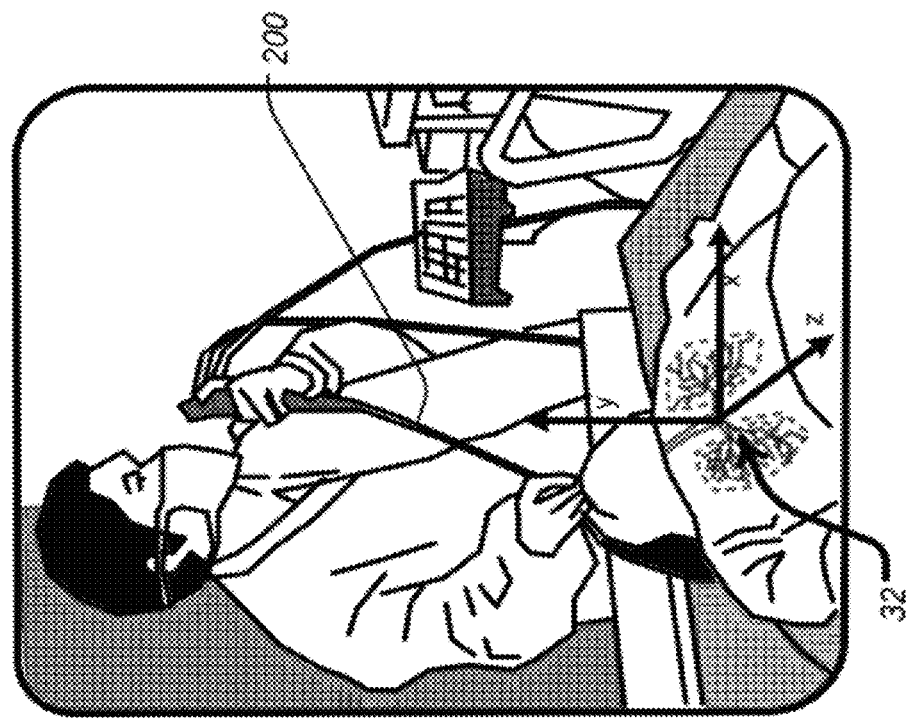
FIGURE 3B
FIGURE 3A

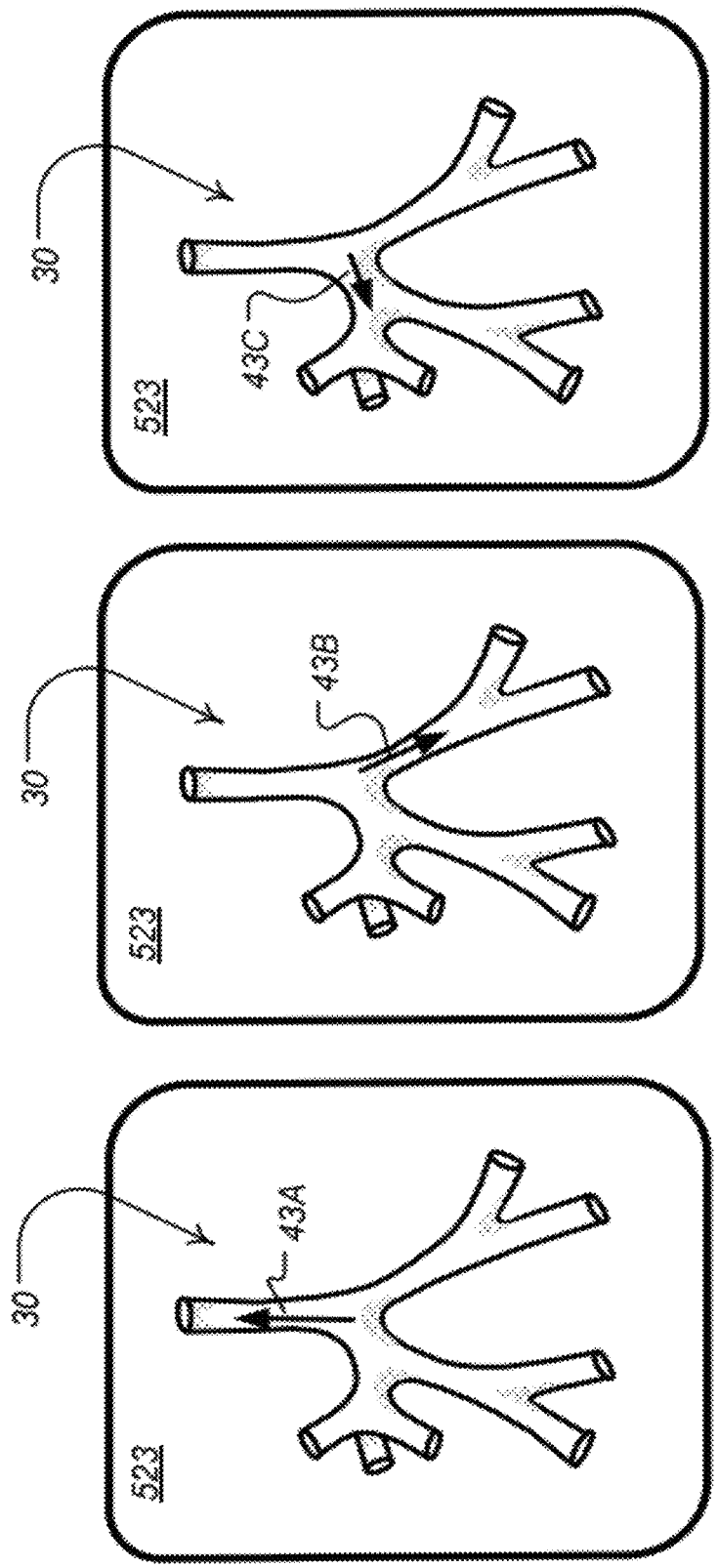

SYSTEMS AND METHODS FOR NAVIGATION WITHIN A BRANCHED STRUCTURE OF A BODY

This application is a continuation of U.S. application Ser. No. 12/043,518, filed Mar. 6, 2008, now U.S. Pat. No. 8,219,179. The referenced application is hereby incorporated by reference in its entirety.

TECHNICAL FIELD

The present invention pertains to interventional medicine and more particularly to systems and methods for navigating a medical instrument within a branched structure of a body.

BACKGROUND

In recent years medical imaging technology, examples of which include, Magnetic Resonance Imaging (MRI) and Computed Tomography (CT) scanning, has been employed to construct patient-specific data bases, from which geometrical three-dimensional models, for example, representative of a structure of one or more organs of a body of the patient, may be generated. Such a model of a bodily structure, for a particular patient, can be employed as a reference during an invasive procedure performed on the patient, for diagnostic and/or treatment purposes, for example, to facilitate navigation of a medical instrument and/or device to a target site within the structure of the patient.

It is almost always necessary that the invasive procedure further employ some kind of real time tracking of the medical instrument within the patient. Many tracking methods employ real time imaging of the instrument and the bodily structure, in which the instrument is being advanced, for example, via fluoroscopy, so that a position of the medical instrument within the structure, as the instrument is being advanced therein, may be directly tracked. However, other tracking methods, which employ a signal transmitter and a sensor attached to the medical instrument, for collecting information defining a position of the instrument, for example, according to magnetic field generating and sensing technologies, provide no overall image or representation of the structure in which the instrument is being advanced, and therefore no context for the positional information collected from the sensor to aid in the navigation of the instrument. In these latter cases, patient-specific data defining a geometric model of the bodily structure may be employed to provide a representation of the structure, onto which the positional information of the sensor may be mapped, in order to provide guidance in navigating the medical instrument. Various methods for real time mapping of this type of positional information onto a representation of a bodily structure, generated from patient-specific data, have been disclosed, but there is still a need for new systems and methods that provide for simpler and less time consuming approaches.

BRIEF DESCRIPTION OF THE DRAWINGS

The following drawings are illustrative of particular embodiments of the disclosure and therefore do not limit the scope of the invention. The drawings are not to scale (unless so stated) and are intended for use in conjunction with the explanations in the following detailed description. Embodiments of the disclosure will hereinafter be described in conjunction with the appended drawings, wherein like numerals denote like elements.

FIG. 3A is a schematic showing the patient undergoing a bronchoscopy procedure.

FIG. 3B is a schematic showing a displayed representation of a model of a bronchial tree structure on a display element of a navigation system, according to some embodiments of the present invention.

FIG. 3C is based on artwork published in Boyden (1955).

FIGS. 4C-E are schematics of the display element of the navigation system presenting a representation of the model of the bronchial tree structure and including indicators for providing instructions to a user of the navigation system, according to some embodiments of the present invention.

DETAILED DESCRIPTION

The following detailed description is exemplary in nature and is not intended to limit the scope, applicability, or configuration of the invention in any way. Rather, the following description provides practical illustrations for implementing exemplary embodiments. Utilizing the teaching provided herein, those skilled in the art will recognize that many of the examples have suitable alternatives that can be utilized.

Figure 1:
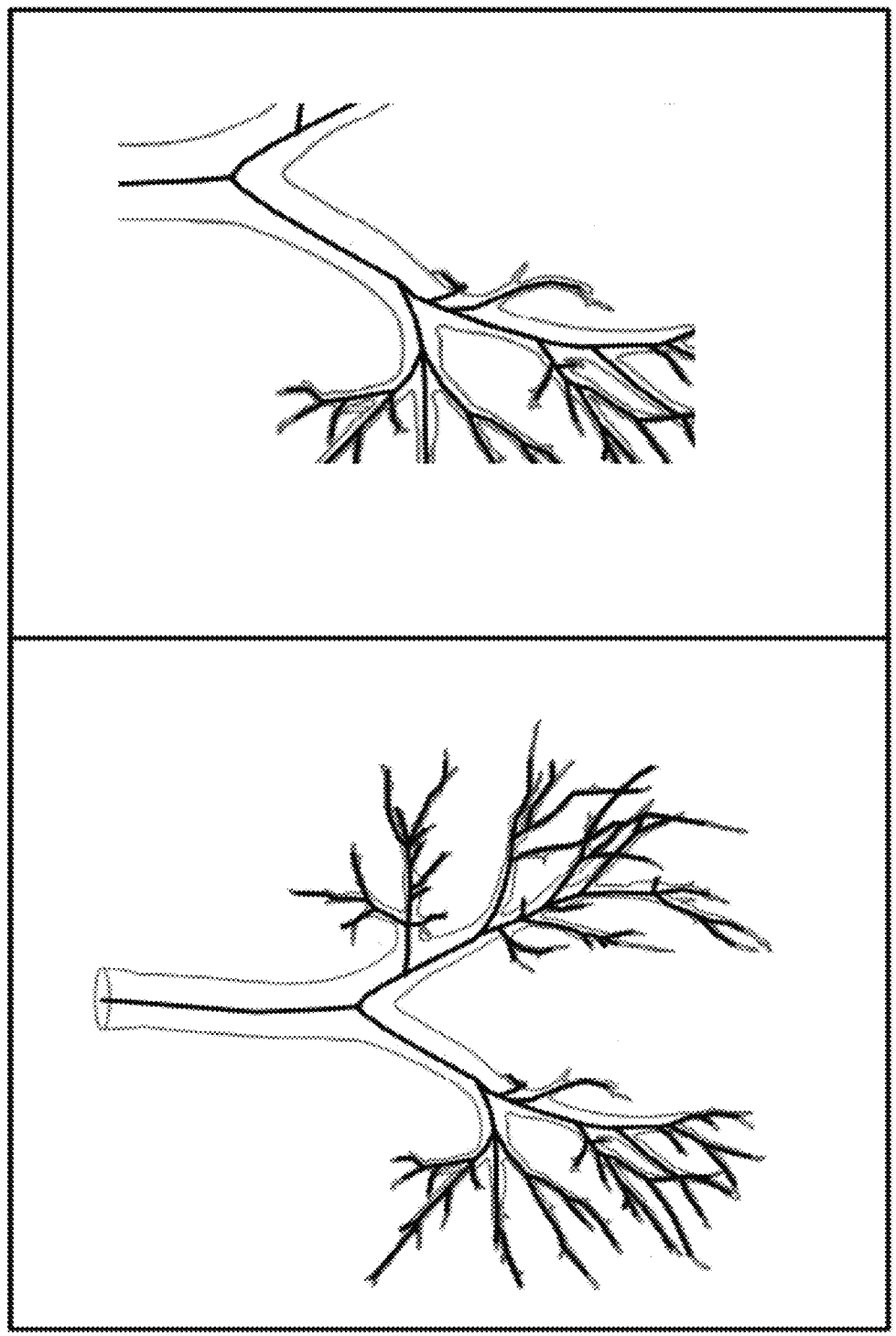
FIG. 1 is an over-all view, alongside a close-up view, of a model of a bronchial tree structure generated from a volumetric data set of images collected via CT scanning of an exemplary patient.

FIG. 1 is an over-all view, alongside a close-up view, of a model of a bronchial tree structure generated from a volumetric data set of images collected via CT scanning of an exemplary patient. FIG. 1 illustrates the model including a surface outline of the tree and a pathway (bolder lines) along branches of the tree, which is defined by predetermined points from the data set, for example, centerline points of the branches of the tree. A subset of the predetermined points defining the pathway, which will be called designated points, include a reference point within a coordinate system of the model and other points, each located at an unique Euclidean distance (i.e. straight line distance) from the reference point, for a given branch of the tree. The model and the predetermined points may be generated from the volumetric data set of the images collected via CT scanning of the bronchial tree according to methods employed by the Pulmonary Workstation of Vida Diagnostics, Inc. (Iowa City, Iowa) and described in the following references, each of which is incorporated herein, by reference: U.S. Patent Publication 2007/0092864, which is entitled: TREATMENT PLANNING METHODS, DEVICES AND SYSTEMS; U.S. Patent Publication 2006/0030958, which is entitled: METHODS AND DEVICES FOR LABELING AND/OR MATCHING; Tschirren et al., *Intrathoracic airway trees: segmentation and airway morphology analysis from low-dose CT scans*. IEEE Trans Med Imaging. 2005 December; 24 (12):1529-39; Tschirren et al., *Matching and anatomical labeling of human airway tree*. IEEE Trans Med Imaging. 2005 December; 24 (12):1540-7; Tschirren, Juerg, *Segmentation, Anatomical Labeling, Branchpoint Matching, and Quantitative Analysis of Human Airway Trees in Volumetric CT Images*, Ph.D. Thesis, The University of Iowa, 2003; Tschirren, Juerg, *Segmentation, Anatomical Labeling, Branchpoint Matching, and Quantitative Analysis of Human Airway Trees in Volumetric CT Images*, Slides from Ph.D. defense, The University of Iowa, 2003; and Li, Kang, *Efficient Optimal Net Surface Detection for Image Segmentation—From Theory to Practice*, M.Sc. Thesis, The University of Iowa, 2003. Although systems and methods are described herein in the context of a bronchial tree, it should be appreciated that the systems and methods may be applied for navigation guidance within any branched structure of a body.

Figure 2:
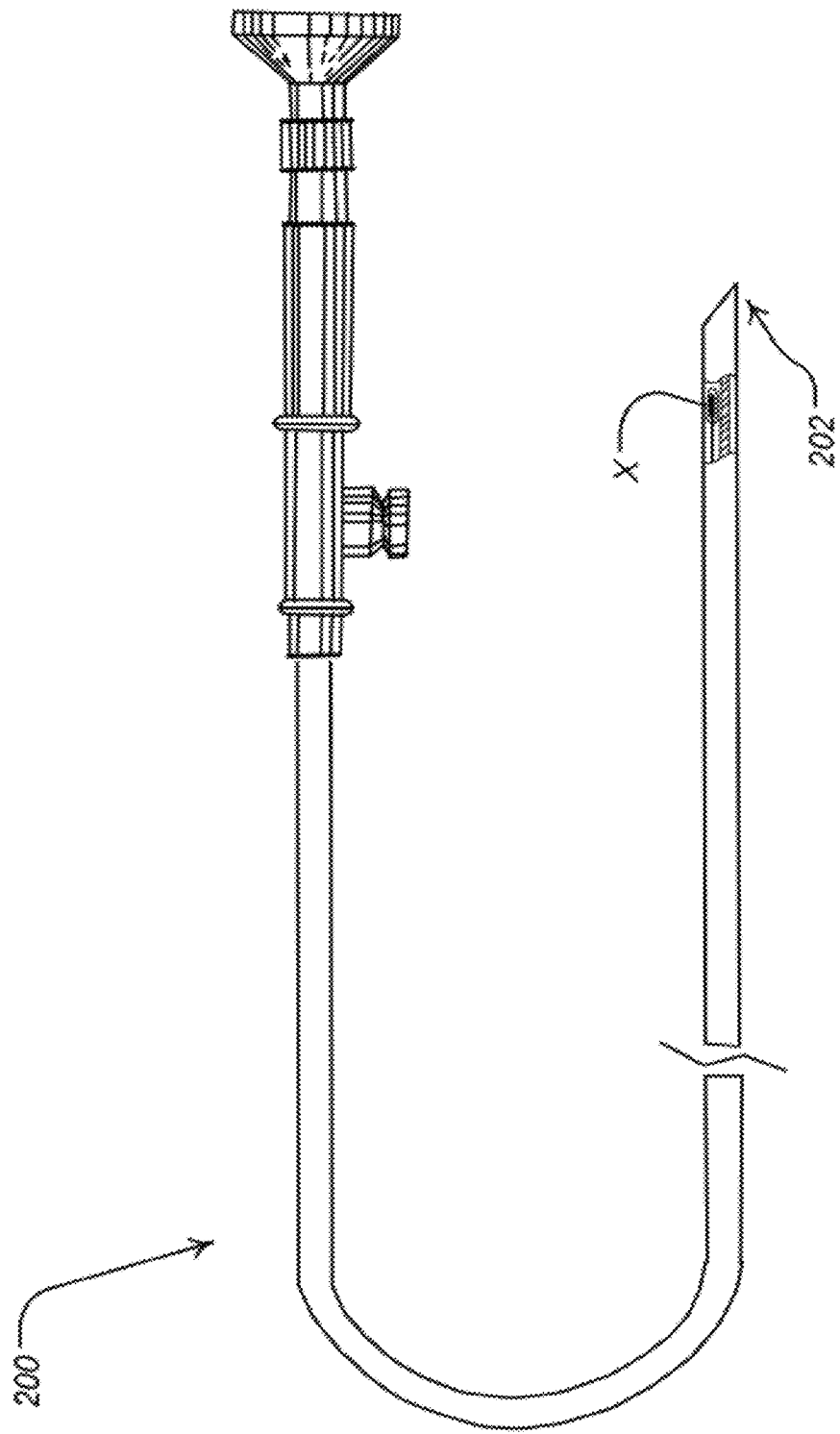
FIG. 2 is a plan view, including a cut-away section, of an exemplary bronchoscope including a tracking sensor.

According to methods of the present invention, the designated points of the predetermined points, which define the pathway, facilitate mapping, onto a display of the model of the tree structure, a tracked location of a medical instrument, in the corresponding actual bronchial tree structure, in real time, during a procedure, in order to provide navigation guidance for the medical instrument. Exemplary types of medical instruments, which may employ methods of the present invention, include, without limitation, diagnostic instruments, such as biopsy tools and bronchoscopes, and treatment instruments, such as tools for deploying stents or valves, or tools that apply ablation energy, for example, for bronchial thermoplasty. FIG. 2 is a plan view, including a cut-away section, of an exemplary bronchoscope 200 including a tracking sensor X attached in proximity to a distal end 202 thereof. According to preferred embodiments of the present invention, tracking sensor X is part of a tracking system 51 (FIG. 5), which employs pulsed DC magnetic fields to track the location of bronchoscope 200 within the actual bronchial tree of the patient; a suitable example of such a system is the microBIRD™ system provided by Ascension Technology Corporation (Burlington, Vt.). It should be noted that any of the other aforementioned types of medical instruments may include tracking sensor X, attached thereto, to track the location thereof within the bronchial tree, as will be described below for bronchoscope 200.

Figure 3C:
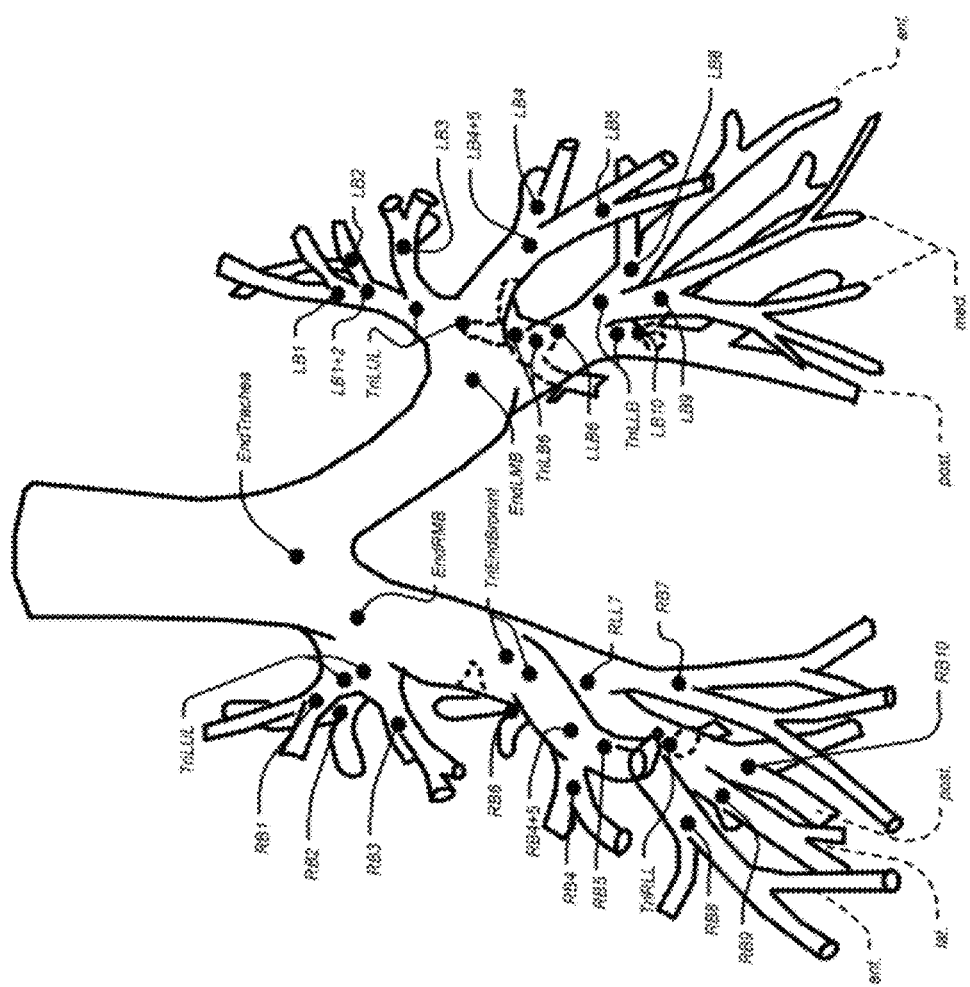
FIG. 3C is a displayed representation of a model of a bronchial tree structure including anatomical labels.

FIG. 3A is a schematic showing the exemplary patient undergoing a bronchoscopy procedure; and FIG. 3B is a schematic showing a displayed representation 30 of the model of the patient's bronchial tree structure presented on a display element 523 of a navigation system workstation 500 (FIG. 5), according to some embodiments of the present invention. Those skilled in the art will appreciate that tracked locations of bronchoscope 200 will be reported by the tracking system as coordinates with respect to a coordinate system 32, which is in a frame of reference of the tracking system and the patient's body, which is within the field of the tracking system, and that the model has a separate frame of reference and a corresponding coordinate system 34, to which tracking coordinate system 32 needs to be registered in order to accurately display representations of locations of bronchoscope 200 on display 30. FIG. 3C is an alternative displayed representation 30' of the model of the patient's bronchial tree structure, which includes anatomical labels. The labels shown in FIG. 3C are based on anatomical identifications, or names for branches of the tree structure, and may have been assigned to branch points of the predetermined points of the model via methods described in the aforementioned patent publication '958, which is incorporated by reference. Alternative display 30', including some or all of the illustrated labels, may be incorporated in place of display 30 in any or all of the embodiments described herein.

With further reference to FIGS. 3A-B, those skilled in the art will appreciate that the operator of bronchoscope 200 may sequentially position bronchoscope 200 within the actual bronchial tree of the patient so that sensor X is located at multiple reference, or fiduciary points, which correspond to known points of the model, and then the coordinates for corresponding points may be used to find a mathematical transformation, for example, an affine transformation, which relates the two frames of reference to one another, thereby registering tracking coordinate system 32 with model coordinate system 34. Although not shown, it should be appreciated that bronchoscope 200 may include a video camera coupled to an imaging system for displaying images of the local environment around distal end 202 of bronchoscope 200, as it is advanced through the bronchial tree of the patient. Although images collected by bronchoscope 200 can help the operator to find the fiduciary points within the patient's bronchial tree, the process of finding the proper points for registration may be cumbersome and time consuming. To simplify the registration process, embodiments of the present invention employ information from the model to facilitate the collection of fiduciary points; for example, as previously described, the information includes the Euclidean distance from a reference point, within model coordinate system 34, for each of the designated predetermined points. For ease of illustration, although not necessarily the case, model coordinate system 34 is shown having an origin located in proximity to the carina of the bronchial tree, so that, in the following discussion, this origin happens to coincide with a reference point M0 of a subset of designated predetermined points M0, M1, M2 and M3, but, it should be noted that, reference point M0 may be located elsewhere, according to alternate embodiments. A sequence of steps for registration, according to some embodiments of the present invention, will now be described in conjunction with FIGS. 4A-B and 5.

Figure 4B:
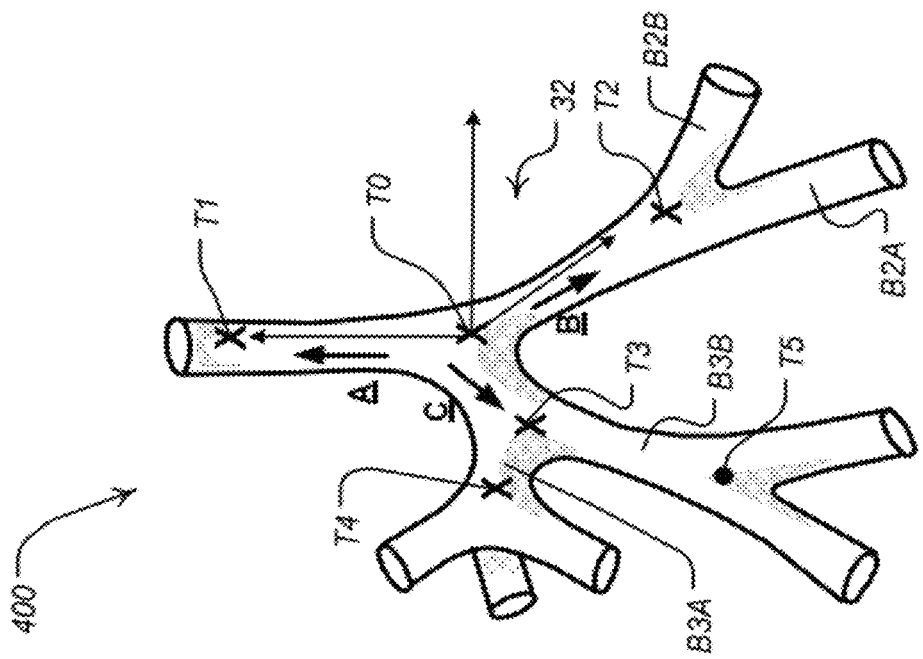
FIG. 4B is a schematic representation of an actual bronchial tree structure of the patient.
Figure 4A:
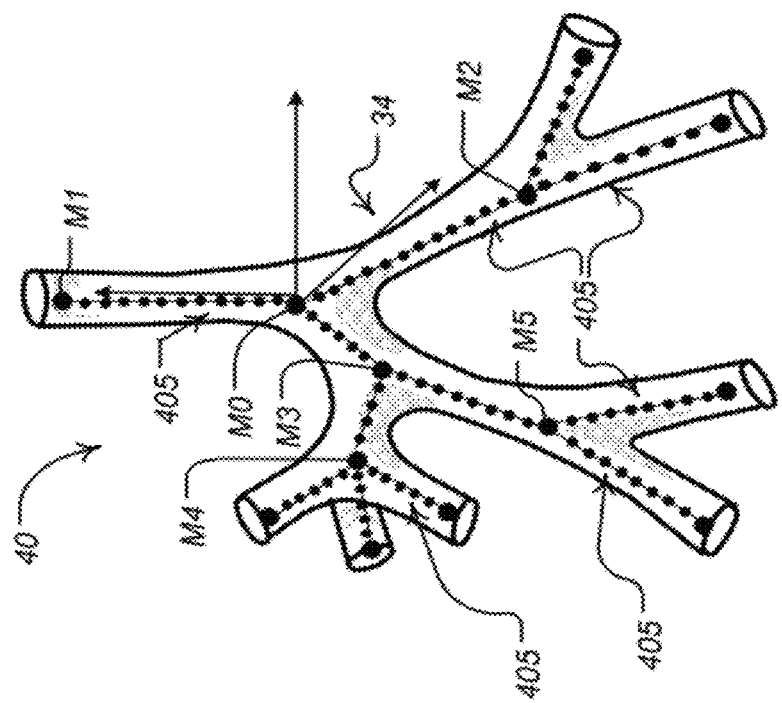
FIG. 4A is a schematic representation of a model of the bronchial tree structure of the patient, the model including predetermined points defining a pathway along branches of the tree, and some designated points of the predetermined points, according to some embodiments of the present invention.
Figure 5:
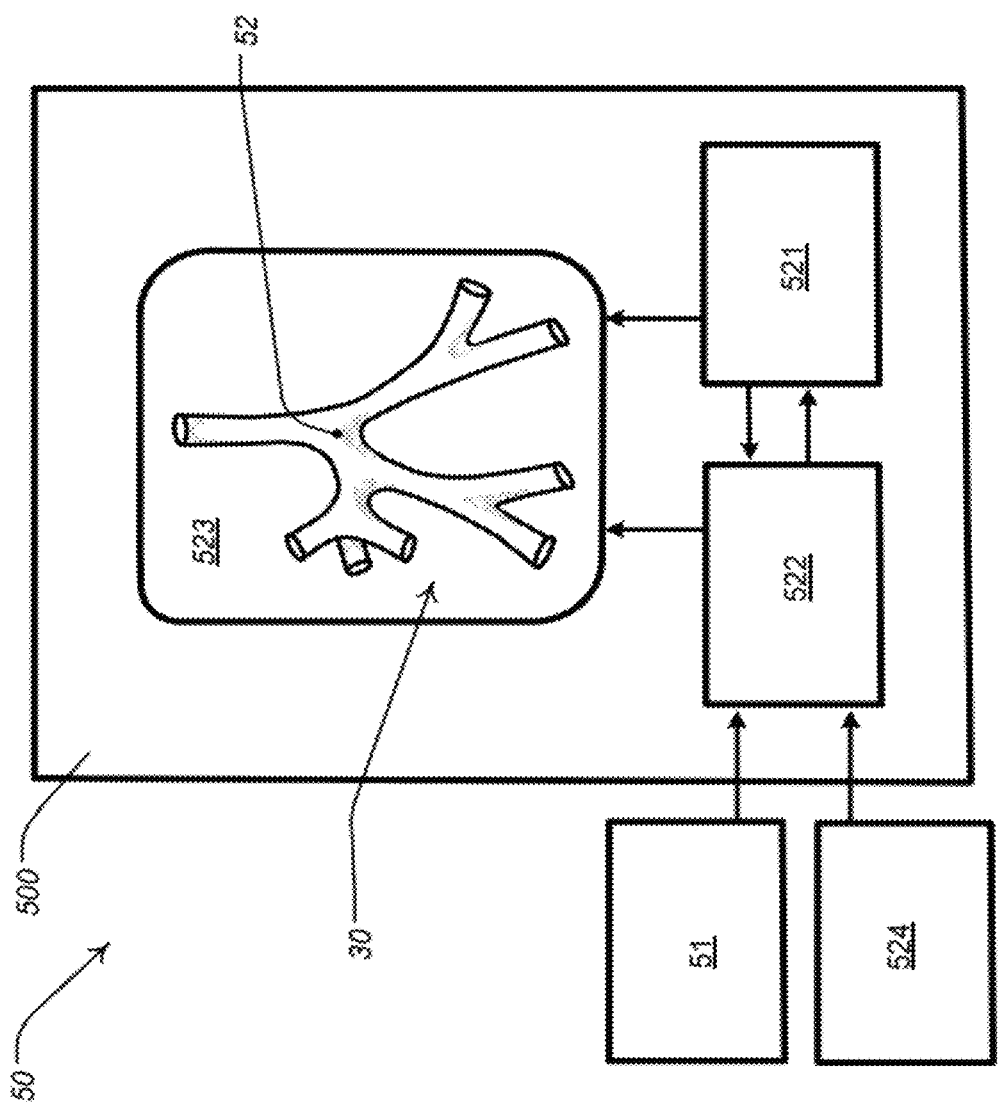
FIG. 5 is a block diagram of a navigation system, according to some embodiments of the present invention.

FIG. 4A is a schematic representation of a model 40 of the bronchial tree of the patient, wherein the model includes predetermined points 405, which define a pathway along branches of the tree, according to some embodiments of the present invention; FIG. 4B is a schematic representation of the actual bronchial tree structure 400 of the patient; and FIG. 5 is a block diagram of a navigation system 50, according to some embodiments of the present invention. According to preferred embodiments of the present invention, each of predetermined points 405 are centerline points along the branches of model 40. With reference to FIG. 5, according to some embodiments, model 40 is stored in a database 521 of workstation 500, which provides input into a processor 522 of workstation 500. FIG. 4A illustrates predetermined points 405 including the subset of designated points identified as M0, M1, M2 and M3; designated point M0, which serves as a reference point of model coordinate system 34, is shown located at a first branching point of a main airway, or trachea, of the tree, in proximity to the carina of the bronchial tree. FIG. 4A further illustrates designated point M0 coinciding with the origin for model coordinate system 34, although this need not be the case in all instances. According to a first step of a method of the present invention, the bronchoscope operator locates bronchoscope 200 in proximity to the carina of the actual bronchial tree 400, so that tracking sensor X is located at a point T0, which corresponds to designated point M0 of model 40, and then instructs processor 522 to establish point T0 as an anchor point of tracking coordinate system 32, via input into workstation 500, for example, at a user interface 524, and, thus, initiates the registration process. Although, for ease of illustration, anchor point T0 is shown as an origin of coordinate system 32, this need not be the case.

According to some embodiments of the present invention, the operator subsequently selects a registration path, for example, a sequence of directions, or branches along which to move sensor X and inputs this information into workstation 500, for example, via user interface 524; according to alternate embodiments, as will be described below in conjunction with FIGS. 4C-E, processor 522 includes a pre-programmed registration path, which is communicated to the operator via display element 523. In either case, as sensor X is moved along the registration path, for example, in each of the three directions, shown by arrows A, B and C, in FIG. 4B, processor 522 receives a stream of positional information from tracking system 51 to calculate Euclidean distances between sensor X and anchor point T0. According to the illustrated embodiment, for each direction A, B, C, when a Euclidean distance of sensor X, from anchor point T0, matches that of a corresponding designated point M1, M2 or M3, from reference point M0, which is stored in database 521 and communicated to processor 522, processor 522 records, or identifies a set of coordinates, in tracking coordinate system 32, for sensor X, located at each of the distances, which are identified, in FIG. 2B, as points T1, T2 and T3. With further reference to FIG. 4A, designated points M2 and M3 are shown approximately corresponding to branching points of the tree structure; although branching points are suitable, and even preferable, locations for designated points M2 and M3, the invention is not so limited, and each of the designated points may be established at any location within tree, as long as the locations have a different Euclidean distance from reference point M0. Furthermore, it should be noted that a suitable registration path need not be limited to the illustrated directions A, B, C, and that registration paths, according to embodiments of the invention, may be broadly defined as including a plurality of non-collinear points that each correspond to any designated point of predetermined points 405.

According to the illustrated embodiment, once the coordinates for each of points T1, T2, and T3 are acquired, tracking coordinate system 32 may be initially registered to model coordinate system 34 by deriving the mathematical transformation relating the model frame of reference to the tracking system frame of reference using the coordinates for each of points T1, T2 T3 and the corresponding coordinates for points M1, M2, M3. Thus, it may be appreciated that the operator of bronchoscope need not look for fiduciary points along the branches of tree 400 because spatial information provided by database 521, in particular, the Euclidean distances between each designated point M1, M2, M3 and reference point M0, is compared with positional information provided by tracking system 51 to automatically collect the fiduciary points.

Turning now to FIGS. 4C-E, which are schematics of display element 532 of navigation system workstation 500, according to some embodiments, an exemplary visual indicator 43A, 43B, 43C is shown overlaid on each displayed representations 30 of the model; indicators 43A, 43B, 43C may provide guidance to a user of the navigation system for carrying out the above-described registration process according to a particular sequence. As previously mentioned, the operator may input a desired sequence at the time of the procedure, or processor 522 may be pre-programmed with instructions for a pre-determined sequence. FIGS. 4C-E illustrate a sequential series of displays 30, presented by display element 532, to guide the bronchoscope operator to move the bronchoscope along branches of the patient's bronchial tree, according to indicators 43A, 43B and 43C, in order to sequentially find points T1, T2 and T3 (FIG. 4B), which correspond to designated points M1, M2 and M3 (FIG. 4A). According to some embodiments, once the operator has moved the bronchoscope far enough in direction A (FIG. 4B), for example to point T1, such that processor 522 has matched the Euclidean distance for sensor X to that of designated point M1, indicator 43A disappears from display 30 and then indicator 43B appears, as shown in FIG. 4D; likewise, once the operator has moved the bronchoscope far enough in direction B, for example to point T2, such that processor 522 has matched the Euclidean distance for sensor X to that of designated point M2, indicator 43B disappears from display 30 and indicator 43C appears, as shown in FIG. 4E, and likewise for movement in direction C. It should be appreciated that additional indicators may also be displayed along each branch, to direct the operator to backtrack the bronchoscope back to anchor point T0, following travel to each of points T1, T2 and T3. Although arrows are illustrated as indicators 43A, 43B, 43C, it should be appreciated that other forms of indicator may be used in alternate embodiments of the invention in order to provide similar guidance in the movement of the bronchoscope, and for providing an indication, or feedback that the bronchoscope has been advanced far enough in each branch; examples of the other forms of indicators include, without limitation, color coding of branches and blinking or flashing points or zones along each branch; alternately words may be used to provide written, explicit instructions and feedback on display 30.

Some embodiments of the present invention encompass navigation methods, which include steps, following an initial registration. With further reference to FIG. 5, once the initial registration is completed, registered sets of coordinates for sensor X are collected from tracking system 51 to track the position of bronchoscope 200, or of another type of medical instrument to which sensor X is attached, on display 30. According to the illustrated embodiment a sphere 52, which is superimposed on display 30, represents a location of the medical instrument that corresponds to a collected registered set of coordinates, which is reported to display element 523 by processor 522 as the medical instrument is moved through the branched structure of the patient. Referring back to FIGS. 4A-B, processor 522 may map the coordinates of sensor X to a closest point of the predetermined points 405, in which case the coordinates of the closest point are reported to display element 523 for positioning of tracking sphere 52; this type of additional processing may compensate for respiratory motion of the patient during navigation, as well as for motion that may be caused by the patient coughing or twitching.

It may be appreciated that tracking is quite accurate for travel between points T1, T2 and T3, and that, although a quality of the registration may deteriorate for travel downstream of points T2 and T3, the registration remains accurate enough for travel through those branches which extend directly downstream from points T2 and T3, for example, branches B2A, B2B, B3A and B3B. According to preferred embodiments, Euclidean distances for each of sensor X positions, collected by tracking system 51, are again calculated by processor 522, when sensor X is moved downstream of either point T2 or T3. For example, when sensor X is moved along branch B3A, processor 522 receives a stream of positional information from tracking system 51 and calculates Euclidean distances between sensor X and anchor point T0, which corresponds to reference point M0; when the processor calculates a distance, for example, for sensor X at a point T4, that is equivalent to a Euclidean distance between a previously designated point M4, of model 40, and reference point M0, as long as the initial registration indicates that sensor X is still located in branch B3A, the coordinates for sensor X, at point T4, along with the coordinates for point M4 are added to the sets of coordinates used for the initial registration to derive another mathematical transformation in order to re-register, or update the previous registration. If point T4 is not reached, and the operator decides to backtrack along branch B3A in order to travel down branch B3B instead, the initial registration will be effective for detecting the new direction from point T3, and will restart distance calculations for positions of sensor X, looking for a match with a distance of a designated point M5 of model 40 from reference point M0. As previously mentioned, designated points M2 and M3 of predetermined points 405 of model 40, are preferably located at branching points, and it may be appreciated that downstream designated points, such as M4 and M5, are also preferably located at branching points, since branching points can serve as effective demarcations for the initiation and termination of each subsequent set of distance calculations, so that, as the bronchoscope is moved deeper into the branching structure 400, and continues to encounter new branching points (this detail is not shown in FIGS. 4A-B, but may be appreciated with reference to FIGS. 1 and 3C), the registration of coordinate systems 32 and 34 can be automatically refined throughout the bronchoscopy procedure, without interruption of navigation guidance provided by navigation system 50 to the operator, for example, via movement of tracking sphere 52 along display 30.

According to some embodiments of the present invention, during navigation of the medical instrument, for example, during a reconnaissance bronchoscopy procedure, processor 522 further measures one or more parameters, which are associated with a group of collected registered sets of coordinates, in order to further enhance navigation guidance. The one or more parameters may include a time that the medical instrument is moved within a particular branch of the branched structure and/or a distance that the instrument is moved along a particular branch of the branched structure; measured parameters may be stored within database 521 for future reference and/or transferred to display element 523 for real time display in conjunction with displayed representation 30 of the model and tracking sphere 52.

Figure 6A:
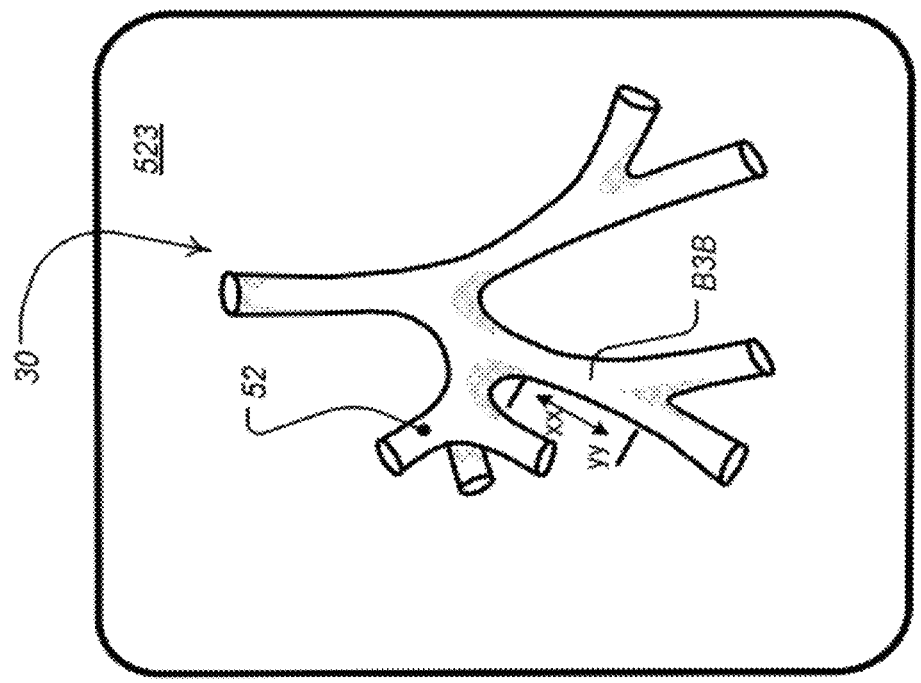
FIGS. 6A-B are schematics of the display element, presenting alternative displays of measured parameters, according to some additional embodiments of the present invention.
Figure 6B:
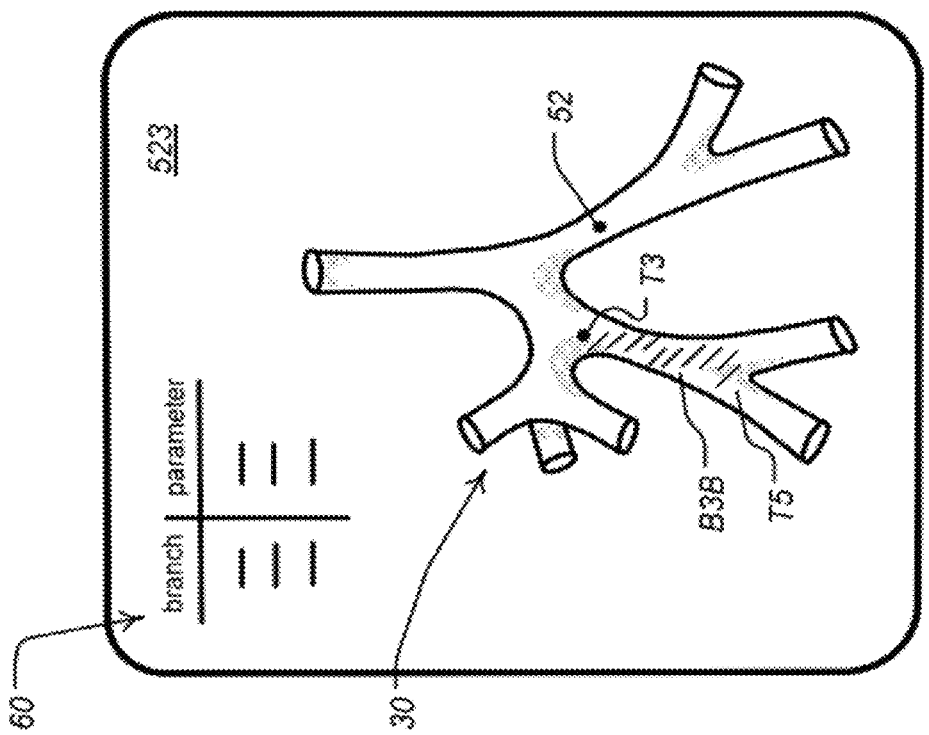

FIGS. 6A-B are schematics of display element 523 presenting alternative displays of measured parameters. FIG. 6A illustrates a tracking sphere 52 on displayed representation 30 of the model, to mark a current position of the bronchoscope, and hatch marks superimposed over branch B3B, as a visual indicator of a distance over which the bronchoscope has previously been moved in branch B3B; of course the visual indicator may be any other type of coding superimposed over branch B3B, for example, color coding. FIG. 6A further illustrates an exemplary table 60 presented on display element 523 which includes a listing of branches in which the bronchoscope has been moved, along with quantities for corresponding measured parameters of travel within each branch, for example, time and distance. According to the illustrated embodiment, as the bronchoscope was moved through branch B3B, registered sets of coordinates were collected for positions of the bronchoscope therein, at least corresponding to branching points T3 and T5, so that processor 522 could calculate, or measure a distance between points T3 and T5, store the distance in database 521, and send the information to display element 523 for recording in table 60 and/or for marking branch B3B. If the bronchoscope had not been moved all the way down branch B3B to point T5, a registered set of coordinates, which corresponds to a point upstream of point T5, within branch B3B, where a direction of the movement of bronchoscope changed, would have been collected and processed, together with the coordinates collected for point T3, to measure and record a shorter distance of travel of the bronchoscope within branch B3B; furthermore, only that portion of branch B3B, which was traveled, would be marked with the visual indicator on display 30. A time of travel within branch B3B may also be measured, stored and recorded/displayed, for example, by starting a timer, or clock when the registered set of coordinates, which corresponds to branching point T3, is collected, upon entry into branch B3B, and, if branching point T5 is not passed (known by an absence of a set of collected registered coordinates corresponding to point T5), stopping the timer when a subsequent collection of a set of coordinates, which also corresponds to point T3, takes place. If a registered set of coordinates, which correspond to point T5, is collected, subsequent to collection of the set for point T3, and the bronchoscope continues to be moved further downstream of point T5, the time between collection of the coordinates for points T3 and T5 may be measured, stored and recorded/displayed. FIG. 6B illustrates an alternative presentation of parameters, wherein the parameters xx and yy, for example time and distance of travel within branch B3B, are displayed on display element 523 at a location alongside branch B3B.

Figure 6C:
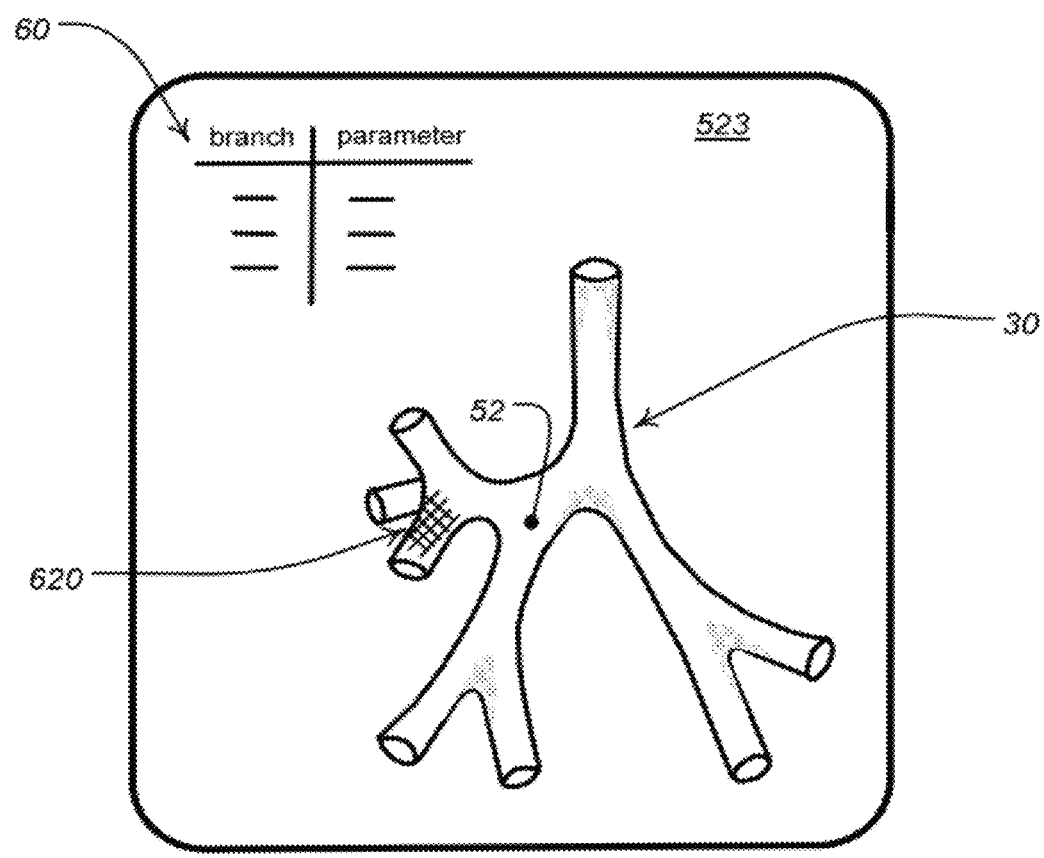
FIG. 6C is a schematic of the display element, presenting the representation of the model of the bronchial tree structure and including an indicator, according to yet further embodiments of the present invention.

As previously described, the medical instrument, which includes sensor X attached thereto, may be one which is adapted to perform a procedure upon the body of the patient, within the branched structure, for example, to take a biopsy sample, deploy a stent, or perform thermoplasty, at a target site. FIG. 6C is a schematic of display element 523, presenting displayed representation 30 of the model and including an indicator, shown with cross-hatching, to mark a site 620 at which the medical instrument performed a procedure, according to yet further embodiments of the present invention. FIG. 6C illustrates tracking sphere 52 as a indicator of a current location of the medical instrument after having been moved away from site 620, upon completion of a procedure at site 620. According to the illustrated embodiment, the indicator at site 620, which may be displayed in any suitable manner and is not limited to the illustrated cross-hatching, serves as a key reference for the operator of the medical instrument, as he or she continues to move the instrument through the branched structure of the patient, for example, to perform another procedure at another site. It should be noted that one of predetermined points 405 of model 40, for example, located just distal to point M4 (FIG. 4A), may be designated, to correspond with site 620, and marked on display 30, with another type of visual indicator, as a reference for navigating the medical instrument to site 620 to perform the procedure, once the registration process is completed.

As described above, bronchoscope 200 may include a video camera, and, according to additional methods of the present invention, alternatively or in addition to the above-described methods, a stream of images is collected from bronchoscope and matched, by processor 522, to virtual endoluminal views, which are also generated from the volumetric data set of the images collected via CT scanning and stored in database 521; the matching may be accomplished, for example, by maximizing a normalized cross-correlation function for the images and the virtual views. This image matching may further refine any of the approaches for registration and/or subsequent navigation, which are described herein, and may help to distinguish between patient motion and bronchoscope motion. Furthermore, because it may be difficult for the bronchoscope operator to advance bronchoscope 200 while maintaining a steady radial position of bronchoscope 200, so that an actual path of bronchoscope 200 approximately corresponds to the pathway defined by predetermined points 405 of model 40, it may be appreciated that the stream of images collected from bronchoscope may further be applied to estimate how far sensor X is shifted off the pathway, defined by predetermined points 405, within a particular branch of the branched structure.

In conclusion, it should be noted that an alternative approach to registration, other than that which was previously described, above, is contemplated. According to the alternative registration method, contours, or trajectories, of actual pathways through the bronchial tree, over which bronchoscope 200 is advanced, are calculated from the positional information provided by tracking system 51 and then matched to characteristic curvatures, or contours, of corresponding portions, or branches, of the pathway defined by predetermined points 405 of model 40. Although FIG. 4A illustrates subsets of predetermined points 405 defining relatively straight line pathway portions in each branch, it should be appreciated, with reference to FIG. 1, that, in actuality, the predetermined points are numerous enough to define uniquely curved pathway portions in each branch. According to an exemplary method, the operator advances bronchoscope 200 in different directions, along a series of bronchial branches, while tracking system 51 collects positional information for sensor X, which positional information is received by processor 522 to calculate trajectories of sensor X for comparison with characteristic contours of the subsets of predetermined points 405 that define portions, or branches, of the pathway of model 40 stored in database 521. Sets of coordinates for locations of tracking sensor X, that are along trajectories matched to the subsets of predetermined points 405, are identified and used with the corresponding predetermined points 405 to find a mathematical transformation, which relates the two frames of reference to one another and thereby register tracking coordinate system 32 with model coordinate system 34. Following this initial registration, during the bronchoscopy procedure, as new branches are encountered by bronchoscope 200, the registration may be automatically updated, or refined, by processor 522 using positional information for tracking sensor X, provided by tracking system 51, as described above for the initial registration. It should be noted that this 'trajectory' approach to registration may be used in conjunction with all, or just a portion of the previously described registration method.

In the foregoing detailed description, the invention has been described with reference to specific embodiments. However, it may be appreciated that various modifications and changes can be made without departing from the scope of the invention as set forth in the appended claims.

We claim:

1. A system for navigating a medical instrument within a branched structure of a body, the system comprising:
    a tracking system configured to collect information defining a position of the medical instrument with respect to a frame of reference of the tracking system; and
    a workstation including a database, a processor and a display, the processor coupled to the database and coupled to the tracking system and configured to receive the positional information therefrom, and the display coupled to the processor;
    the database configured to receive and store a data defining a geometrical model of the branched structure including coordinates for predetermined points, with respect to a model coordinate system in a frame of reference of the geometric model, the predetermined points defining a registration pathway along branches of the geometric model of the branched structure and including a first designated point, serving as a reference point for the model coordinate system, and a plurality of other designated points;
    the processor adapted to:
        receive input for establishing an anchor point of a coordinate system for the frame of reference of the tracking system, the anchor point corresponding to the first designated point of the pathway;
        convert the positional information, collected by the tracking system, into Euclidean distances of the medical instrument from the established anchor point of the tracking coordinate system;
        transmit instructions to the display to display a visual indicator to a user of a direction to move the medical instrument to positions corresponding to the plurality of other designated points, wherein the processor is adapted to determine the direction to move the medical instrument by using the Euclidean distances of the medical instrument from the established anchor point;
        register the tracking coordinate system to the model coordinate system by deriving a mathematical transformation, which relates the model frame of reference to the tracking frame of reference, using the positional information from the tracking system and the corresponding coordinates of the plurality of other designated points;
    the display adapted to receive instructions to from the processor to display the visual indictor and to display the visual indicator.

2. The system of claim 1 wherein the visual indicator comprises an arrow.

3. The system of claim 1 wherein the visual indicator comprises a plurality of visual indicators displayed consecutively as the user moves the medical device to positions corresponding to the plurality of other designated points.

4. The system of claim 3 wherein the visual indicators change when the processor detects that the medical instrument has reached a position corresponding to one of the other designated points.

5. The system of claim 4 wherein the visual indicators direct a user to backtrack the medical instrument when a position corresponding to one of the other designated points is reached which is a furthest designated point within an airway branch.

6. The system of claim 1 wherein the processor is further adapted to direct the display to display a visual representation of the geometric model, and wherein the visual indicator is displayed on the visual representation of the geometric model.

7. The system of claim 6 wherein the visual indicator comprises an arrow within the geometric model, wherein the arrow directs the user to move the medical instrument within the branched structure toward a position corresponding to one of the plurality of other designated points.

8. The system of claim 1 wherein the registration pathway comprises a first point located along a first branch of the geometric model, a second point located along a second branch of the geometric model, and a third point located along a third branch of the geometric model.

9. The system of claim 8 wherein the processor is further configured to identify a Euclidean distance from the anchor to each of the first, second, and third points.

10. The system of claim 8 wherein the processor is preprogrammed with the registration pathway.

11. The system of claim 8 further comprising a user interface, wherein the user interface is configured to transmit the registration pathway from the user to the processor when the user selects the registration pathway.

12. The system of claim 8 wherein the processor is further configured to direct the display to display an indication to the user that the medical device has been advanced far enough within each branch of the branched structure corresponding to the first, second and third branches of the geometric model.

13. A method for registering a branched structure of a body to a geometric model of the branched structure, the method comprising:
  advancing a medical instrument including a tracking sensor in the branched structure in a tracking coordinate system, wherein the medical instrument is in communication with a system comprising a database, a processor, a user interface and a display, the database comprising data defining the geometrical model of the branched structure including predetermined points defining a registration pathway along branches of the geometric model of the branched structure and including a first designated point, serving as a reference point for the model coordinate system, and a plurality of other designated points;
  inputting an indication that the medical instrument is located at an anchor point when the medical instrument is at the anchor point, wherein the anchor point is a position in the branched structure corresponding to the reference point;
  observing a first visual indicator on the display indicating a direction in which to move the medical device to a position corresponding to one of the plurality of designated points;
  advancing the medical instrument to the position corresponding to one of the plurality of designated points by moving the medical device as directed by the first visual indicator;
  observing a second visual indicator on the display indicating a direction in which to move the medical device to a position corresponding to another one of the plurality of designated points;
  advancing the medical instrument to the position corresponding to another one of the plurality of designated points by moving the medical device as directed by the second visual indicator;
  wherein the processor converts positional information, collected by the tracking system, into Euclidean distances of the medical instrument from the established anchor point of the tracking coordinate system, directs the display to display the visual indicators, and registers the tracking coordinate system to the model coordinate system by deriving a mathematical transformation, which relates a frame of reference of the geometric model to a frame of reference of the tracking system, using the positional information from the tracking system and the corresponding coordinates of the plurality of other designated points.

14. The method of claim 13 wherein the visual indicators comprise arrows.

15. The method of claim 13 further comprising selecting a registration pathway and inputting the registration pathway into the system.

16. The method of claim 13 further comprising observing a third visual indicator, between the first visual indicator and the second visual indicator, indicating a direction in which to move the medical device wherein the direction is backward within the branched structure; and retracting the medical instrument away from the position corresponding to one of the plurality of designated points by moving the medical device as directed by the third visual indicator.

17. The method of claim 13 wherein the processor further directs the display to display a visual representation of the geometric model, and wherein the processor further directs the display to display the visual indicators on the visual representation of the geometric model.

18. The method of claim 13 wherein the visual indicator comprises an arrow within the geometric model, wherein the arrow directs the user to move the medical instrument within the branched structure toward a position corresponding to one of the plurality of other designated points.

* * * * *